US008953858B2

(12) United States Patent
Becker et al.

(10) Patent No.: US 8,953,858 B2
(45) Date of Patent: Feb. 10, 2015

(54) METHODS AND SYSTEMS FOR ANALYZING, PRIORITIZING, VISUALIZING, AND REPORTING MEDICAL IMAGES

(75) Inventors: Moshe Becker, Los Gatos, CA (US); Hayit Greenspan, Los Gatos, CA (US); Eliahu Konen, Tel-Aviv (IL); Arnaldo Mayer, Herzellya (IL)

(73) Assignees: Radlogics, Inc., Los Gatos, CA (US); Tel Hashomer Medical Research and Infrastructure and Services Ltd., Ramat-Gan (IL)

( * ) Notice: Subject to any disclaimer, the term of this patent is extended or adjusted under 35 U.S.C. 154(b) by 80 days.

(21) Appl. No.: 13/575,841

(22) PCT Filed: Jan. 28, 2011

(86) PCT No.: PCT/US2011/023059
§ 371 (c)(1), (2), (4) Date: Oct. 22, 2012

(87) PCT Pub. No.: WO2011/094639
PCT Pub. Date: Aug. 4, 2011

(65) Prior Publication Data
US 2013/0039552 A1 Feb. 14, 2013

Related U.S. Application Data

(60) Provisional application No. 61/299,309, filed on Jan. 28, 2010.

(51) Int. Cl.
*G06K 9/00* (2006.01)
*G06F 19/00* (2011.01)
*G06Q 50/00* (2012.01)

(52) U.S. Cl.
CPC .......... *G06F 19/321* (2013.01); *G06F 19/3487* (2013.01)
USPC ................................ 382/128; 382/209; 705/3

(58) Field of Classification Search
USPC ......... 382/100, 103, 106–107, 128–134, 162, 382/168, 173, 181, 189–190, 209, 219, 232, 382/254, 274, 276, 286, 305, 312; 705/3; 378/4, 21
See application file for complete search history.

(56) References Cited

U.S. PATENT DOCUMENTS

| 6,574,357 B2 | 6/2003 | Wang |
| 6,925,200 B2 | 8/2005 | Wood et al. |

(Continued)

FOREIGN PATENT DOCUMENTS

| JP | 2006-260301 A | 9/2006 |
| JP | 2006-271541 A | 10/2006 |

OTHER PUBLICATIONS

European search report and opinion dated Jul. 25, 2013 for EP Application No. 11737791.1.

(Continued)

*Primary Examiner* — Seyed Azarian
(74) *Attorney, Agent, or Firm* — Wilson Sonsini Goodrich & Rosati

(57) ABSTRACT

Methods and systems for retrieving and processing medical diagnostic images are provided, comprising using picture analysis prioritization visualization and reporting system ("PAPVR system") to determine whether each of one or more images from an image database or imaging device is of medical interest to a reviewing physician, determine whether one or more of the images is representative of the images, and provide the one or more images to a display and analysis system for review by a reviewing physician. The PAPVR system can provide the one or more images with a Key Image that is representative of the images. In addition, the PAPVR system can detect whether a patient suffers from a particular ailment, and provide a reviewing physician quantitative information that is relevant to the patient's condition.

20 Claims, 11 Drawing Sheets

(56) References Cited

U.S. PATENT DOCUMENTS

| | | |
|---|---|---|
| 7,184,582 B2 * | 2/2007 | Giger et al. .................. 382/128 |
| 7,738,684 B2 * | 6/2010 | Kariathungal et al. ....... 382/128 |
| 7,756,309 B2 * | 7/2010 | Gholap et al. ................ 382/128 |
| 7,995,815 B2 | 8/2011 | Nekrich |
| 8,331,637 B2 * | 12/2012 | Bar-Aviv et al. .............. 382/128 |
| 8,538,776 B2 * | 9/2013 | Reiner ............................. 705/3 |
| 2003/0095692 A1 | 5/2003 | Mundy et al. |
| 2004/0247166 A1 | 12/2004 | Giger et al. |
| 2006/0139318 A1 | 6/2006 | Kariathungal et al. |
| 2007/0041623 A1 | 2/2007 | Roehrig et al. |
| 2007/0092142 A1 | 4/2007 | Kuriathungal et al. |
| 2008/0215525 A1 | 9/2008 | Kakimoto et al. |
| 2008/0275736 A1 | 11/2008 | Lei |
| 2008/0298665 A1 | 12/2008 | Kariathungal et al. |
| 2009/0024418 A1 | 1/2009 | Yu |
| 2009/0132279 A1 | 5/2009 | Yeluri |
| 2012/0041786 A1 * | 2/2012 | Yu ..................................... 705/3 |

OTHER PUBLICATIONS

Sinha, et al. A review of medical imaging informatics. Annals of the New York Academy of Sciences. 2002; 980:168-197.

International search report and written opinion dated Aug. 2, 2011 for PCT/US2011/023059.

\* cited by examiner

METHODS AND SYSTEMS FOR ANALYZING, PRIORITIZING, VISUALIZING, AND REPORTING MEDICAL IMAGES

CROSS-REFERENCE

This application claims the benefit of U.S. Provisional Patent Application Ser. No. 61/299,309, filed on Jan. 28, 2010, which is entirely incorporated herein by reference.

FIELD OF THE INVENTION

This application generally relates to medical imaging; more particularly, this invention relates to systems and methods for analyzing, prioritizing, visualizing and reporting medical images.

BACKGROUND OF THE INVENTION

Medical imaging systems, such as computerized tomography ("CT") scanners and magnetic resonance imaging ("MRI") scanners, allow a physician to examine a patient's internal organs and areas of the patient's body that require a thorough examination for medical treatment. In use, a visualizing scanner outputs two-dimensional ("2D") and three-dimensional ("3D") medical images that can include a sequence of computerized cross-sectional images of a certain body organ, which is then interpreted by reviewing physician, such as a specialized radiologist.

Commonly, a patient is referred for a visual scan by a general practitioner or an expert (or specialized) practitioner. A series of 2D and sometimes 3D medical images (or scans) are subsequently obtained. The scan is then forwarded to a reviewing physician (such as a radiologist) who is responsible for the analysis and diagnosis of the scan. Radiologists are typically trained to analyze medical images from various parts of a patient's body, such as medical images of the brain, abdomen, spine, chest, pelvis and joints. After a radiologist (or other reviewing physician) analyzes the medical images, he or she prepares a document ("Radiology Report") that includes radiological findings, and sometimes key images from the scan that best show the findings. The radiology report is then sent back to the referring practitioner.

In most hospitals and radiology centers, the scan is transferred to a picture archiving communication system ("PACS") before being accessed by the radiologists. A PACS is a computer system that acquires, transmits, stores, retrieves, and displays digital images and related patient information from a variety of imaging sources and communicates the information over a network. Many hospitals are also equipped with a radiology information system ("RIS")—used by radiology departments to perform patient tracking and scheduling, result reporting and image tracking. Medical images are typically stored in an independent format, such as a Digital Imaging and Communications in Medicine ("DICOM") format. Electronic images and reports are transmitted digitally via PACS, which eliminates the need to manually file, retrieve or transport film jackets. A PACS typically includes four components: the imaging modalities, such as computer axial tomography ("CAT") or CT, MRI, position emission tomography ("PET"), or PET/CT; a secured network for the transmission of patient information; workstations for interpreting and reviewing images; and long and short term archives for the storage and retrieval of images and reports.

There are image retrieval and processing systems and methods available in the art. For example, U.S. patent application Ser. No. 12/178,560 to Yu ("Yu"), entitled "SYSTEMS FOR GENERATING RADIOLOGY REPORTS," which is entirely incorporated herein by reference, teaches a method for generating a patient report, comprising presenting an operator with an on screen menu of standardized types of reports and having the operator select a standardized type of report from the on screen menu of standardized types of reports. Yu further teaches presenting the operator with an on screen organ list corresponding to the selected standardized type of report; for each organ, presenting the operator with a menu of standard medical descriptions corresponding to the organ; and having the operator determine a medical description corresponding to each organ. Yu teaches outputting a patient report describing the medical description of each organ.

As another example, U.S. patent application Ser. No. 11/805,532 to Nekrich ("Nekrich"), entitled "RADIOLOGY CASE DISTRIBUTION AND SORTING SYSTEMS AND METHODS," which is entirely incorporated herein by reference, teaches a system and method for processing an image, including a means for receiving image information, a means for queuing the image information, and a means for receiving profile information for a plurality of image analysts. The system of Nekrich can further include a means for selecting an image analyst from the plurality of image analysts by comparing the image information from the profile information.

As another example, U.S. patent application Ser. No. 12/224,652 to Bar-Aviv et al. ("Bar-Aviv"), entitled "SYSTEM AND METHOD OF AUTOMATIC PRIORITIZATION AND ANALYSIS OF MEDICAL IMAGES," which is entirely incorporated herein by reference, teaches a system for analyzing a source medical image of a body organ. The system of Bar-Aviv comprises an input unit for obtaining the source medical image having three dimensions or more, a feature extraction unit that is designed for obtaining a number of features of the body organ from the source medical image, and a classification unit that is designed for estimating a priority level according to the features.

While current medical image retrieval and processing systems have provided physicians tremendous capabilities in storing and retrieving medical images, there are limitations associated with these systems. For instance, for a typical scan, a hospital may obtain hundreds of images, and a reviewing physician might not have time to review each of the images to determine whether a patient has a particular type of medical condition. In cases in which a hospital scans several patients in a relatively short period of time, the hospital might not have the resources to timely review each patient's medical images to determine whether a physician should review the image further, and whether the patient has a particular type of medical condition. In addition, modern medical imaging systems can operate much more quickly than older systems, which has led to a decrease in the time it takes to generate a scan. While a shorter scan time could be beneficial for providing rapid patient care, it has resulted in the generation of a significant amount of data that must be compiled, analyzed and presented to a reviewing physician. Further, modern medical imaging systems can operate at higher resolutions, resulting in increased number of higher resolution two-dimensional images and/or three-dimensional images (or scans thereof). As the time to generate scans decreases and the number of scans (and images obtained) per patient increases, hospitals without sufficient resources might not be able to review each image and provide patients with medical care in an accurate and efficient manner. Further, while some hospitals might have medical imaging, processing and retrieval systems for handling scans, current systems are not capable of accurately and efficiently prioritizing scans. In addition, current systems do not provide scan reviewing and patient treating physicians with the capability to acquire accurate patient-specific diagnostic information from each of the images or scans.

Accordingly, there is a need in the art for improved imaging, analysis, prioritization and reporting systems. In particular, there is a need in the art for methods and systems for accurately and efficiently analyzing and prioritizing medical images, such as images acquired from CT scans and MRIs, to provide better patient risk management.

SUMMARY OF THE INVENTION

In an aspect of the invention, computer-implemented methods for providing medical diagnostic images and enhanced report capabilities are provided.

In one embodiment, a computer-implemented method for providing medical diagnostic images comprises using a computer system to retrieve one or more images from an image database or an imaging device (e.g., imaging modality), the one or more images defining a set of images; using the computer system to determine whether each of the images is of medical interest to a reviewing physician; using the computer system to determine whether one or more of the images is representative of the set of images; and providing the one or more images to a display and analysis system for review by a reviewing physician, wherein the one or more images are provided with an image that is representative of the set of images.

In another embodiment, a computer-implemented method for providing enhanced report capabilities for medical diagnostic images comprises retrieving one or more images from an image database or an imaging device, the one or more images defining a set of images; determining whether each of the images is of medical interest to a reviewing physician; determining whether one or more of the images is representative of the set of images; providing the one or more images to a display and analysis system for review by a reviewing physician; and providing one or more text blocks associated with items determined to be of medical interest, the one or more text blocks for being mixed, matched and edited by a reviewing physician to create a report.

In another aspect of the invention, a system for visualizing and reporting patient-specific medical information comprises an imaging modality for retrieving medical diagnostic images from a patient; a reviewing system for displaying medical images to a reviewing physician; a prioritization visualization and reporting system in communication with the imaging modality and the reviewing system, wherein the prioritization visualization and reporting system is for retrieving one or more images from the imaging modality, the one or more images defining a set of images, determining whether each of the images is of medical interest to a reviewing physician, determining whether one or more of the images is representative of the set of images and providing the one or more images to the reviewing system, wherein the one or more images are provided with an image that is representative of the set of images.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the invention will be obtained by reference to the following detailed description that sets forth illustrative embodiments, in which the principles of the invention are utilized, and the accompanying drawings of which:

DETAILED DESCRIPTION OF THE INVENTION

Figure 1:
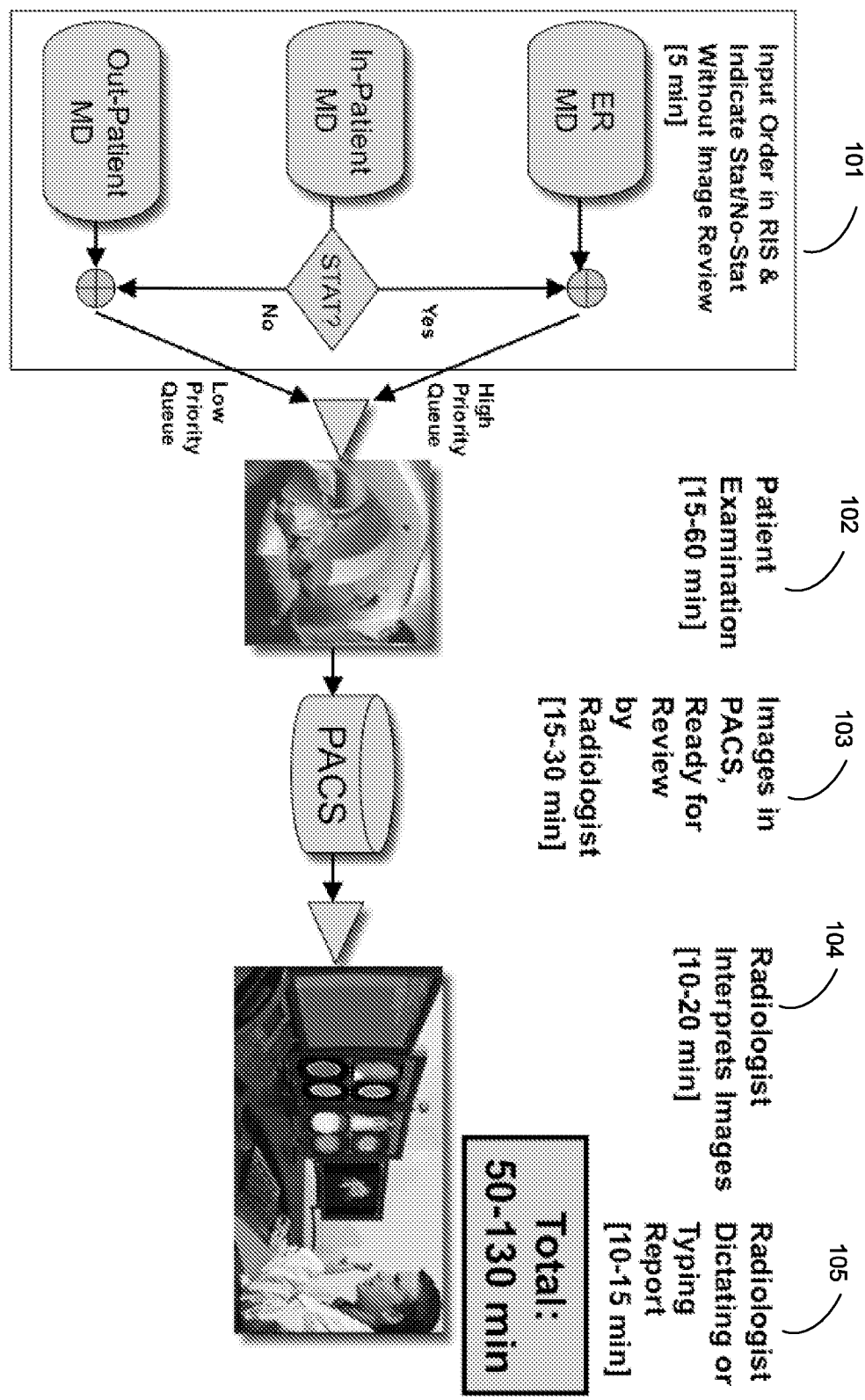
FIG. 1 shows a medical imaging workflow with a timeline, in accordance with an exemplary embodiment of the current art.

While various embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

The invention provides methods and systems for analyzing and prioritizing medical images, and for reporting medical findings. For example, an analysis of medical images according to some aspects of the system and methods disclosed herein may be used to identify critical medical conditions, and, based on this analysis, said system and method may further be used to organize a work list for a reviewing physician based on the severity of the medical findings and to then create a text document that lists the medical findings in the analyzed medical images. For example, a database may be created, showing a "normalized" version of each possible aspect of a region. Accordingly, deviations above a certain threshold may be used to flag a certain image. Furthermore, in some areas, just the appearance of an unexpected presence (for example, a liquid in the pleural space) may be used to flag an image or a series of images. It is clear that many variations can be done without changing the spirit of the invention. Various aspects of the invention described herein may be applied to any of the particular applications set forth below or for any other types of displays, or radiological data management applications. The invention may be applied as a standalone system or method, or as part of an integrated software package, such as a medical and/or laboratory data management package or application, or as part of an integrated picture archiving communication systems ("PACS") solution. It shall be understood that different aspects of the invention can be appreciated individually, collectively, or in combination with each other.

Current medical imaging, processing and retrieval systems are incapable of providing sufficient patient risk management. This is due at least in part to the lack of case prioritization. In addition, hospitals may not have the resources to review and analyze each medical image in a set of medical images in a timely manner, and current PACS do not provide physicians the resources to efficiently and accurately analyze, prioritize, and report findings in medical images.

In embodiments of the invention, methods and systems are provided for efficiently and accurately interpreting medical images, acquiring quantitative measurements for each of the medical images, and providing the reviewing physicians the capability to generate medical reports. Methods and systems of embodiments of the invention can provide hospitals with the capability to streamline their medical image processing, which advantageously reduces the time and resources necessary to review each scan (e.g., CT/CAT, MRI, PET/CT) associated with a subject (e.g., patient), and provide physicians accurate data necessary to provide adequate medical care.

In embodiments of the invention, methods and systems are provided for analyzing medical images (e.g., CT scans of the chest, abdomen, and head). Methods and systems of embodiments of the invention improve the quality of patient care by automatically prioritizing cases prior to review by a reviewing physician or specialist (e.g., radiologist) based on pathological findings. In various embodiments, methods and systems for analyzing and prioritizing medical images generate preliminary reports, which are available to reviewing physicians as they open cases for review. This advantageously reduces the time it takes a radiologist to prepare a final report. The report can include additional information, such as quantified measurements (e.g., cross-sectional areas, volumes) automatically extracted, generated, or calculated from the data. Methods and systems of embodiments of the invention can seamlessly integrate into an existing radiological workflow.

Reference will now be made to the figures. It will be appreciated that the figures are not necessarily drawn to scale.

With reference to FIG. 1, a typical medical imaging workflow as currently used is shown. Approximate lengths of time associated with each step in the workflow are also indicated in the figure. Such times are provided by way of example only. It will be appreciated that other times are possible.

Initially, in step 101, a patient is admitted to a hospital or other healthcare provider for treatment or a routine checkup. For example, the patient may be admitted through the emergency room ("ER"), the in-patient unit, or the out-patient unit of a healthcare provider. An admitting physician or nurse conducts a preliminary examination of the patient to determine whether the patient's condition warrants immediate medical attention (i.e., "Stat" or "No-Stat"). For instance, the admitting physician can determine whether the patient's condition is of high or low priority. The admitting physician or nurse may indicate the patient's status (e.g., high priority, low priority) in a patient tracking system, such as the patient tracking feature of a radiology information system ("RIS"). The admitting physician or nurse can also indicate "Stat" or "Non-Stat" (or "No-Stat"). Cases indicated as "Stat" may be placed in a high priority queue while cases indicated as "No-Stat" can be placed in a low priority queue.

With continued reference to FIG. 1, in a patient examination step 102, medical images (e.g., CAT/CT scan, MRI, PET/CT scan) are obtained from a patient. Medical images may be obtained using a variety of methods. For example, a three-dimensional image (with 2-D cross-sections) of a particular region of a patient's body may be obtained using a CT scanner. As another example, a three-dimensional image may be obtained using an MRI. Such three-dimensional image may have two-dimensional cross-sectional images. Alternatively, multiple images may be provided, whether they originate from a three-dimensional image or not. Medical images (or scans) thus obtained are stored in a PACS. The PACS makes these images available for review by a reviewing physician or specialist (e.g., radiologist).

Next, in step 103, a radiologist retrieves and interprets the images obtained during the patient examination step. The radiologist reviews all of the images in a case in step 104.

In the next step 105, the radiologist prepares a report having the radiologist's analysis of the patient's medical images. The radiologist might dictate (or type) a report comprising the radiologist's diagnosis of the patient's condition. The radiologist may add to the report images taken from the case that show visual representation of the diagnosis ("Key Images"). The radiologist can then make the report available for review by a referring physician.

Picture Analysis Prioritization Visualization and Reporting System

In an aspect of the invention, a computer system is provided for improving the efficiency and accuracy of a workflow process. In embodiments of the invention, the computer system, which, for example, could be a standard personal computer with a standard CPU, memory and storage, is an enhanced picture archiving communication system, or an add-on subsystem to an existing PACS and/or RIS. In embodiments of the invention, the computer system can be configured to analyze and prioritize images and patient cases. The computer system can be referred to as a picture analysis prioritization visualization and reporting system (also "PAPVR system" herein). The computer system can automatically retrieve medical images from an imaging modality (e.g., CAT/CT scanner, MRI, PET/CT scanner) or a database in which medical images are stored, or a PACS, automatically analyze the medical images, and provide the medical images and the results of the analysis for review by a reviewing or referring physician, or a specialist, such as a radiologist.

Figure 2:
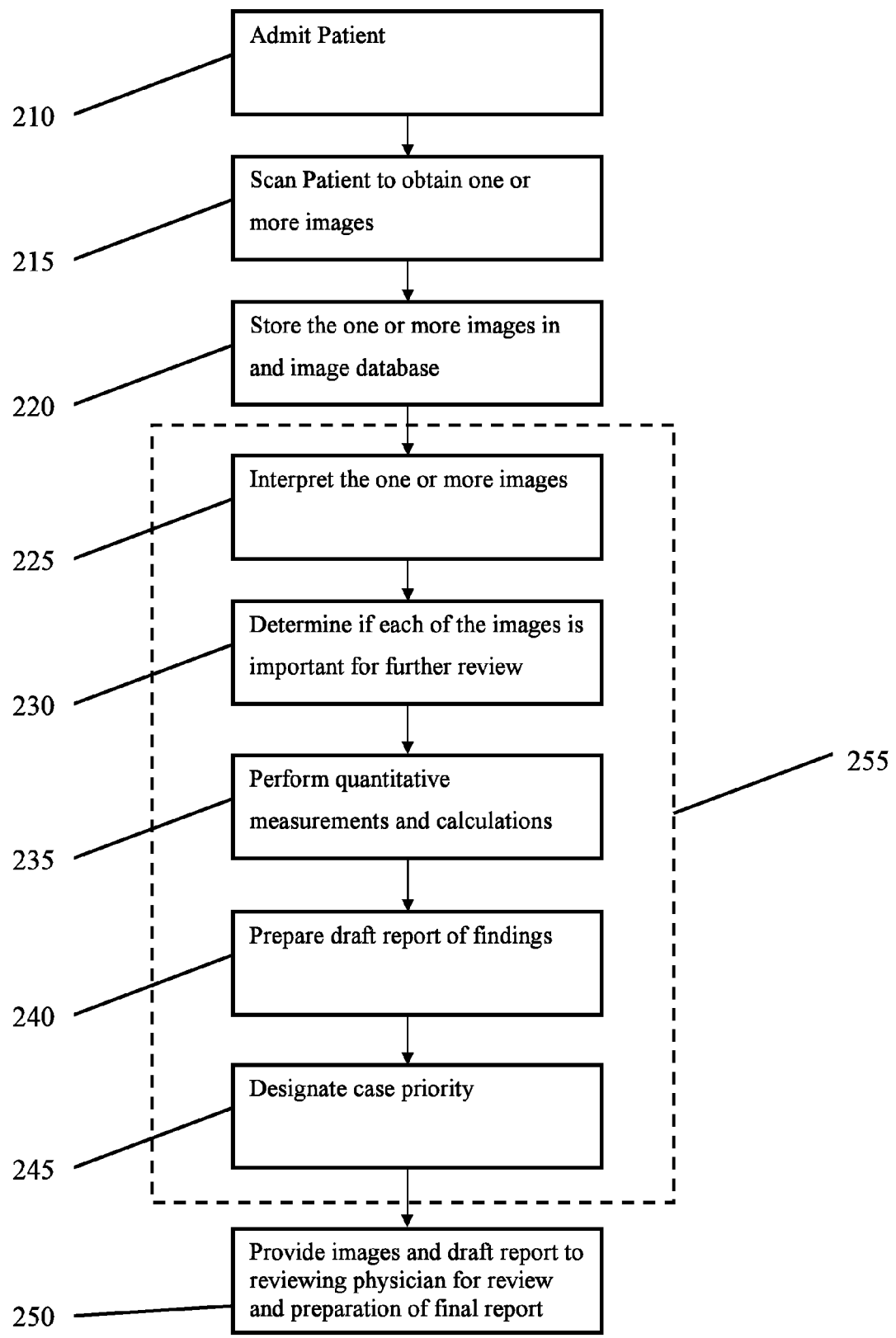
FIG. 2 shows an examination workflow, in accordance with an embodiment of the invention.

With reference to FIG. 2, an examination workflow is illustrated, in accordance with an embodiment of the invention. In a first step 210, a patient is admitted for treatment or a routine checkup. An admitting physician or nurse can determine whether the patient's condition is of high priority or low priority. Next, in step 215 a predetermined region of the patient's body is scanned. In an embodiment, a predetermined region of the patient's body is imaged using CT (or CAT) scan. In another embodiment, a predetermined region of the patient's body can be imaged using MRI, PET scan, or PET/CT scan. Scanning the patient can provide one or more images (e.g., 2-D or 3-D images) of a predetermined region of the patient's body. Next, in step 220 the one or more images (or set of images) are stored in an image database. In an embodiment, the image database can be a subsystem of a PACS. In another embodiment, the image database can be a standalone computer system. In such a case, the standalone computer system can be in communication with a PACS.

With continued reference to FIG. 2, in step 225, the one or more images are analyzed by a PAPVR system (or enhanced PACS), in accordance with an embodiment of the invention. In an embodiment, a subset of the one or more images is analyzed and interpreted by the PAPVR system. Next, in step 230, the PAPVR system reviews the one or more images to determine whether the one or more images would be of interest (e.g., Key Images) to a reviewing or referring physician. This can entail determining whether the one or more images show any abnormalities with respect to the patient's condition, for example, free pleural air (pneumothorax) or fluid, aortic dissection, intracranial hemorrhage, liver metastases etc. These various conditions, for example, can be determined using comparable images, as well as comparing them to normalized images as described throughout herein. In an embodiment, the PAPVR system can determine whether each or a subset of the one or more images is important for further review by a reviewing or referring physician. In some cases, further the system may perform additional analysis, including but not limited to providing quantitative measurements, as well as, in some cases, the indication of the localization (for example with an added color overlay that can be turned off for better viewing, or other suitable methods) where the measurement has been performed. This localization is more specific than a keyframe as it may be a small region inside a key frame. For example, When we detect blood in the pleural effusion (hemothorax), we can highlight the areas where blood was detected into the pleural effusion. This can save time in some cases since if blood is detected correctly somewhere in the pleural effusion and the radiologist is brought automatically to that place for verification, the radiologist can diagnose the hemothorax without further measuring liquid intensity in other slices.

Next, in step 235, the PAPVR system can perform quantitative measurements and calculations (e.g., distances, cross-sectional areas, volumes), that is relevant to the patient's condition, for example, measuring the volume of air in a pneumothorax by doing image analysis as described herein. Next, in step 240, the PAPVR system can create a draft report that includes the findings, calculations and Key Images. Next, in step 245, the PAPVR system can designate case priority. Next, in step 250, the PAPVR system can provide the one or more images and the draft report for review and preparation of the final report by a reviewing or referring physician. In an embodiment, the one or more images can be provided with the PAPVR system's interpretation of the one or more images. The steps 225, 230, 235, 240 and 245 can be collectively referred to as step 255.

Further, in some cases, the system could be automatically comparing the present study with a previous similar study obtained on the same patient in the past; in these cases the invention can compare findings and quantify changes such as increased pleural fluid or increased dilatation of an aortic aneurysm which has significant clinical implications.

In an aspect of the invention, methods for retrieving and processing medical diagnostic images are provided. The methods comprise using a computer system, such as an enhanced picture archiving communication system (also "picture archiving communication and analysis system" herein), to retrieve one or more images (e.g., two-dimensional images from a three-dimensional scan) from an image database or directly from an imaging device (e.g., imaging modality). In an embodiment, the one or more images define a set of images. Next, the computer system determines whether each of the images is of medical interest to a reviewing physician, for example, by identifying the image that shows the point in which the aorta is seen at its widest diameter, or, for example, by analyzing that specific aspect in a series of volumetric images and calculating the value, and then flagging the one with the largest numeric value, either by dimension, area or any other suitable measure. In an embodiment, this can include the computer system comparing each of the images to images from patients with known medical conditions. Next, the computer system determines whether one or more of the images is representative of the set of images and designates them as Key Images. The computer system then provides the one or more images to a display and analysis system for review by a reviewing physician. In addition, using the above image comparisons, the computer system can detect whether a patient suffers from a particular ailment, and provide a reviewing physician quantitative information (e.g., distances, cross-sectional areas, volumes), that is relevant to the patient's condition.

In an aspect of the invention, a PAPVR system is provided for automatically retrieving, reviewing and analyzing one or more medical images acquired from an imaging modality. In embodiments, the PAPVR system can analyze and interpret each or a subset of one or more images acquired by an examination system, such as an imaging modality (e.g., CAT/CT scan, MRI, PET/CT scan). In some case, the PAPVR system can be referred to as an enhanced or improved PACS. The PAPVR system of preferable embodiments can automatically perform step 255 of FIG. 2.

In preferable embodiments of the invention, the PAPVR system is configured to automatically detect and quantify various physiological features or abnormalities, for example, by using image processing algorithms that identify the pneumothorax condition, and other image processing algorithms that can segment the area of the pneumothorax and calculate its volume, as discussed exemplarily throughout this document. By automatically detecting various physiological features or abnormalities, the PAPVR system of embodiments of the invention can advantageously reduce the time and resources required to review images provided from an imaging modality (e.g., CT scan, MRI, PET/CT). This increases the accuracy of detection and quantification, and provides for improved patient care and more efficient workflow. PAPVR systems of embodiments of the invention advantageously enable healthcare providers to provide patients with accurate and rapid patient care.

Figure 3:
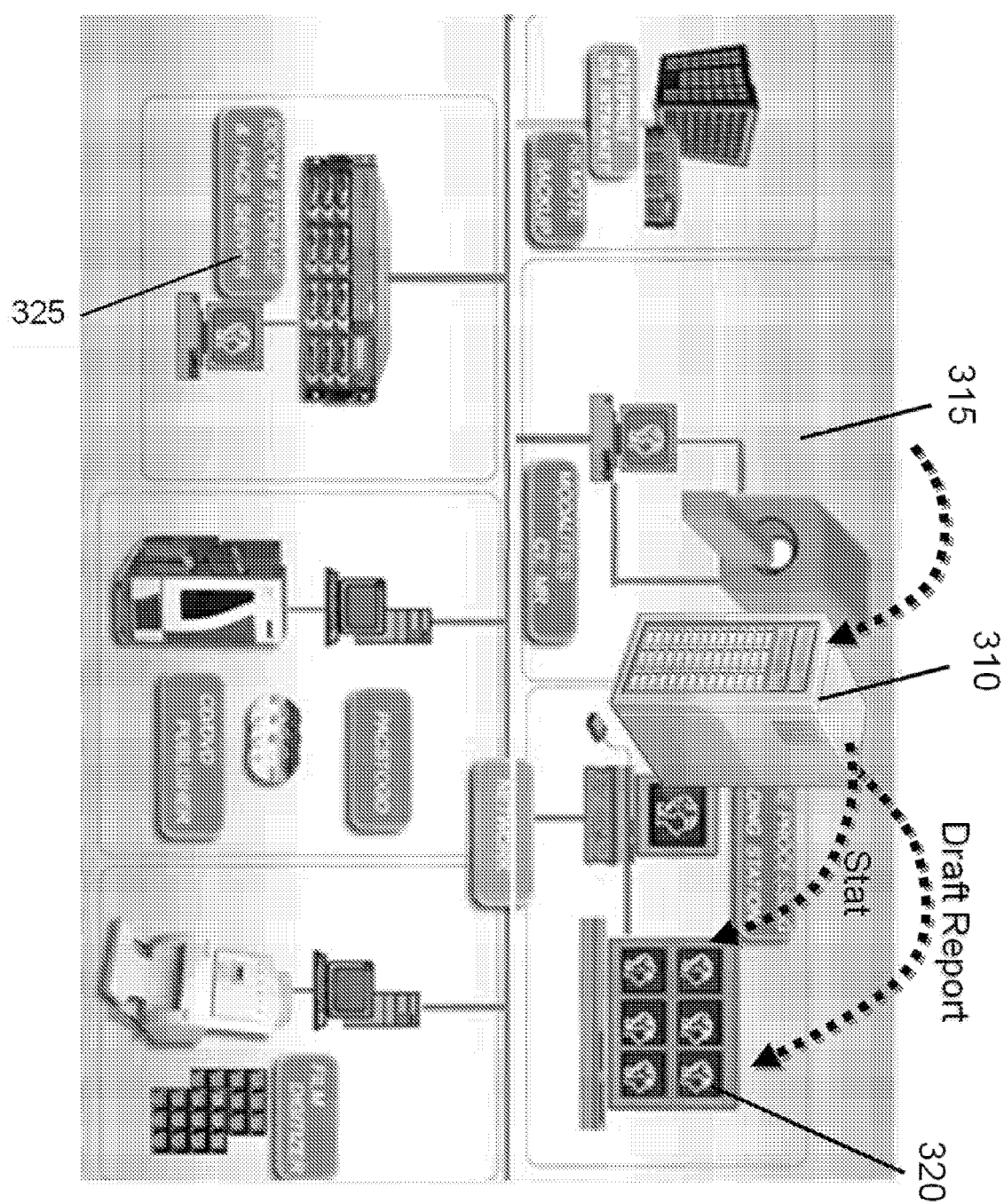
FIG. 3 shows a picture analysis prioritization visualization and reporting ("PAPVR") system as part of a workflow system, in accordance with an embodiment of the invention.

With reference to FIG. 3, in an embodiment of the invention, a PAPVR system 310 configured to retrieve, analyze and interpret one or more images provided by an examination system is illustrated, in accordance with an embodiment of the invention. The PAPVR system 310 can include tangible, non-transitory computer readable media. The PAPVR system 310 can be part of a healthcare provider's workflow. In an embodiment, the PAPVR system can automatically perform step 255 of FIG. 2. The PAPVR system 310 can retrieve images from a storage unit that can be part of the PAPVR system 310, or from a separate PACS system 325, and prepare the images for review. The PAPVR system 310 can be in communication with other components or computer systems (also "systems" herein) of a healthcare provider. In an embodiment, the PAPVR system 310 can be physically situated at the location of a healthcare provider (i.e., the PAPVR system can be on-site). In such a case, the PAPVR system can communicate with other components or systems of the healthcare provider via the healthcare provider's network, such as an intranet. In another embodiment, the PAPVR system 310 can be an off-site system that communicates with other components of a healthcare provider via the Internet or World Wide Web.

With continued reference to FIG. 3, the PAPVR system 310 is configured to retrieve one or more images from an examination system 315 or a PACS 325; analyze and interpret (also referred to as "process" herein) some or all of the one or more images; and provide the one or more images for review by a referring or treating physician. In an embodiment, following processing, the PAPVR system 310 can provide the images to a reviewing system 320 configured to display the images to a physician. In an embodiment, the PAPVR system 310 can analyze and interprets each cross-section of a three-dimensional scan of a particular region of a patient's body. The PAPVR system may contain, receive, or utilize computer readable media, which may contain instructions, logic, data, or code that may be stored in persistent or temporary memory of a computer, or may somehow affect or initiate action by the PAPVR systems, or any computers or servers contained therein. Any steps or analysis described herein may be performed by utilizing such computer readable media.

In embodiments, the PAPVR system 310 can automatically detect various physiological features, again, for example, by using image processing algorithms that identify the pneumothorax condition, and another image processing algorithm that can segment the area of the pneumothorax and calculate its volume. For example, the PAPVR system can automatically detect air and/or liquid pockets and quantify (or calculate) the volume of the air and/or liquid pockets. The PAPVR system can also quantify cross-sectional areas and distances. In some embodiments, the PAPVR system can detect bones and organs, and quantify the cross-sectional areas and/or volumes of the bones and organs.

In embodiments, the PAPVR system 310 can provide additional data with each of the one or more images. The PAPVR system 310 can provide the additional data for review by a reviewing or referring physician (using the reviewing system 320, for example). The additional data can include distances (e.g., distances between features) cross-sectional areas, gas (e.g., air) volumes, liquid (e.g., blood) volumes, blood vessel cross-sectional measurements, location and number of bone fractures, and shift in the position of body organs such as the mediastinum in tension pneumothorax. In an embodiment, when a physician accesses each of the one or more images, the additional data is made accessible to the physician. In an embodiment, when the physician views a two-dimensional cross-sectional image of a three-dimensional image, the additional data is provided with each two-dimensional cross-sectional image. In some embodiments, additional data may be provided with each image by way of metadata associated with each image.

With continued reference to FIG. 3, the PAPVR system 310 can be in communication with other systems or components associated with the healthcare provider's workflow system. In embodiments, the PAPVR system 310 can be in communication with one or more of an imaging modality (e.g., CAT/CT scan, MRI, PET/CT scan) remote backup system, a DICOM storage and PACS server 325, a PACSToGO system, a CD/DVD publishing system and a film digitizer. The PAPVR system 310 can be in communication with other workflow systems and/or components via an intranet, the Internet (e.g., wired or wireless web), or other mode of communication, such as Bluetooth. In certain embodiments, the PAPVR system can be configured to interact manually or automatically with one or more systems or components associated with a workflow system.

Figure 4:
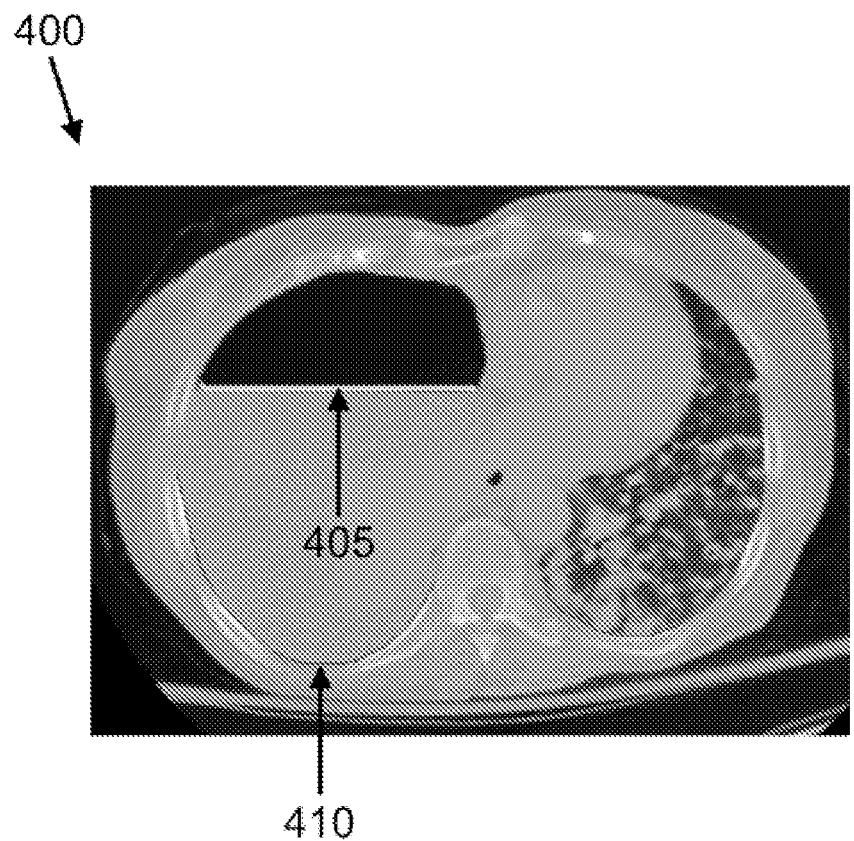
FIG. 4 shows a CT scan of a patient's pleural cavity, in accordance with an embodiment of the invention.

FIG. 4 shows one image of a CT scan 400 processed by a PAPVR system of embodiments of the invention. The image 400 is a two-dimensional cross-sectional image of a patient's pleural cavity. The image 400 is one example of an image among many images that can be provided from a CT scan. The CT scan shows free pleural effusion, free pleural air and mediastinal shift (=tension hydropneumothorax) 405 and the patient's rib cage 410. In embodiments, the PAPVR system is configured to automatically detect a pleural effusion and quantify the volume of free liquid and free air in the patient's pleural cavity and identify the mediastinal shift which suggest a medical emergency. In an embodiment, the PAPVR system can also automatically detect the presence of an air volume or space (e.g., pneumo-thorax) and quantify the volume. In some embodiments, the PAPVR system can automatically detect and quantify various physiological features or abnormalities, such as, e.g., pneumothorax, tension pneumothorax, pleural effusion, ascending and descending aortic caliber and aortic dissections.

Key Image

In an aspect of the invention, a PAPVR system can be configured to provide a radiologist or other reviewing physician with one or more images, Key Images that are representative of a set of images and/or representative of the patient's condition.

Figure 5:
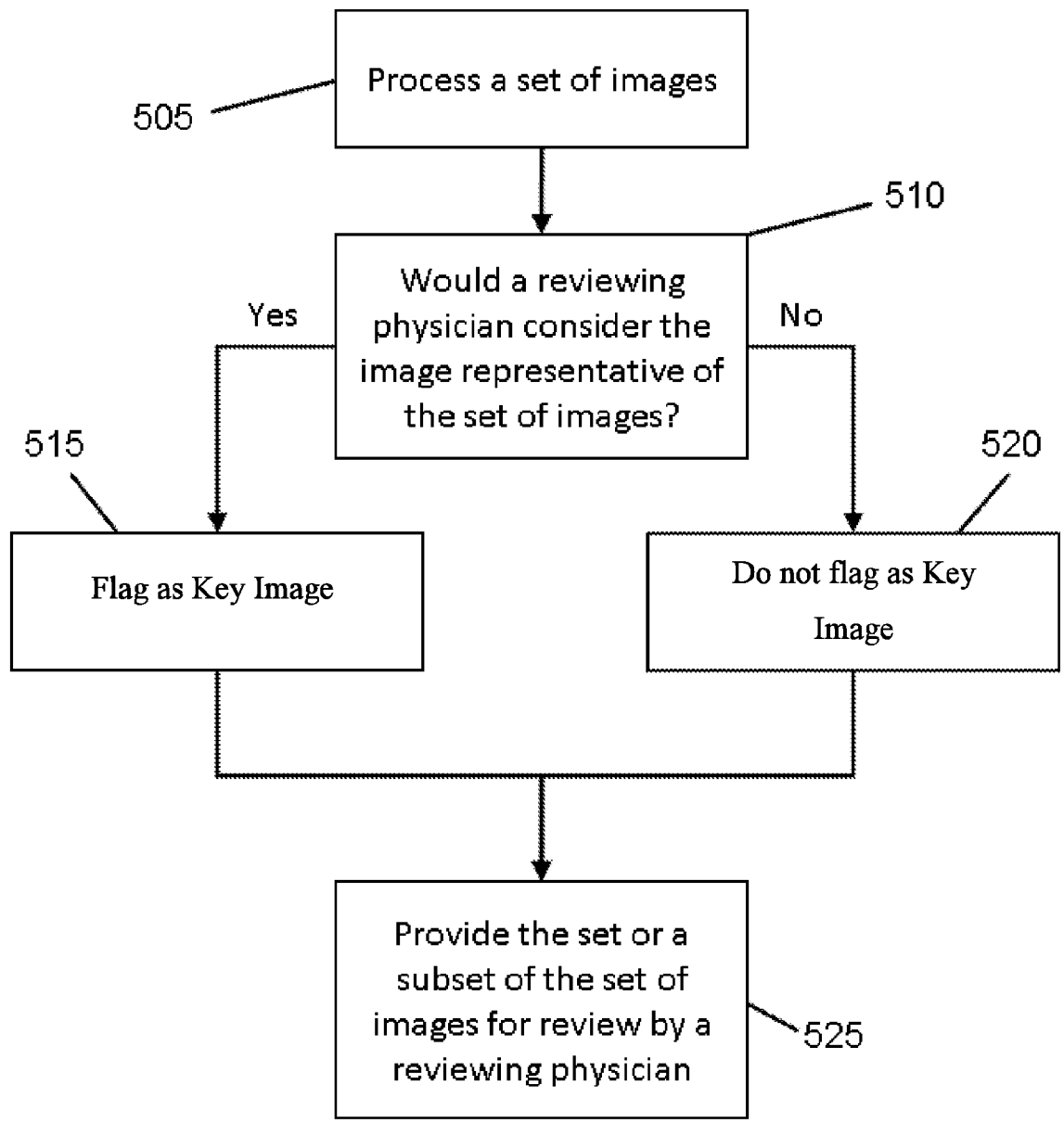
FIG. 5 shows steps taken in flagging an image as a representative image, in accordance with an embodiment of the invention.

With reference to FIG. 5, in an embodiment, a PAPVR system can automatically identify one or more images as Key Images, based on, for example, the image that shows the aorta at its widest. In an embodiment, a Key Image is an image that is representative of a set of images. In another embodiment, a Key Image is representative of the patient's condition. In such a case, the Key Image can best capture the patient's condition. In some cases, the Key Image can accurately define a set of images. For instance, if a patient's CT scan shows a pleural effusion, the Key Image can be the image (e.g., two-dimensional cross-sectional image) determined by the PAPVR system to clearly and accurately show the pleural effusion. In some embodiments, when the PAPVR system provides one or more images and data for review by a reviewing (such as a radiologist) or referring physician, the Key Image can be the first image the reviewing physician observes. In other embodiments, the Key Images provided by the PAPVR system can be the images used by the reviewing physician in the final report prepared for the referring physician. For example, a Key Image can be found by comparing tissue density of certain sections with average examples (i.e., liquids have a different density than "normal tissue") or structural abnormalities, such as "speckles" of another density, which could indicate for example tumors, or fracture lines in a bone, etc.

With continued reference to FIG. 5, in a first step 505, the PAPVR system retrieves an image (e.g., two-dimensional cross-section of a three-dimensional image or scan) for processing. Next, in step 510, the PAPVR system determines whether a reviewing physician would consider the image representative of the set of images. If the image is determined to be representative of the set of images, in step 515 the image is flagged as a "Key Image." If the image is determined to not be representative of the set of images, in step 520 the image is not flagged as a "Key Image." Next, in step 525, the set of images or a subset of the set of images is provided to a reviewing (or treating) physician for review. In an alternative embodiment, if an image is not found to be representative, the PAPVR system can skip step 515 and proceed directly to step 525.

Image Prioritization

In an aspect of the invention, a PAPVR system can automatically prioritize an image. Image prioritization can advantageously reduce time and resources required by a reviewing or treating physician to make an accurate diagnosis. In some embodiments, the PAPVR system can flag some images as having a higher priority relative to other images, and a physician or radiologist can review only those images, thus saving considerable time in analyzing images associated with a particular scan.

A PAPVR system of embodiments of the invention can automatically prioritize an image. In an embodiment, the PAPVR system can be configured to flag an image as having a "high priority" or a "low priority." In other embodiments, the PAPVR system can flag an image as having high, medium or low priority. In an embodiment, the PAPVR system can categorize an image among a predetermined number of categories. For example, one, two, three, four, five, six, seven, eight, or more categories may be utilized. In still other embodiments, the PAPVR system can assign a numerical value (e.g., 1-10, 1-100, 1-1000, 1-10,000) to an image that is indicative of the priority of the image. For example, a high priority image can be assigned a numerical value of 1, while a low priority image can be assigned a numerical value of 100. In some embodiments, the user can specify how an image is to be prioritized. For example, the user can specify that images are to be prioritized as high, medium, or low priority.

In some embodiments, a user (e.g., a reviewing/referring physician, radiologist) can request that the PAPVR system only provide images having a priority that is above a minimum (or cut-off) priority. For example, the user can request that the system provide only high priority images for review. As another example, the user can request that the PAPVR system provide images having a priority numerical value above a certain value or within a certain range. In some embodiments, the user can specify the minimum (cut-off) priority.

Figure 6:
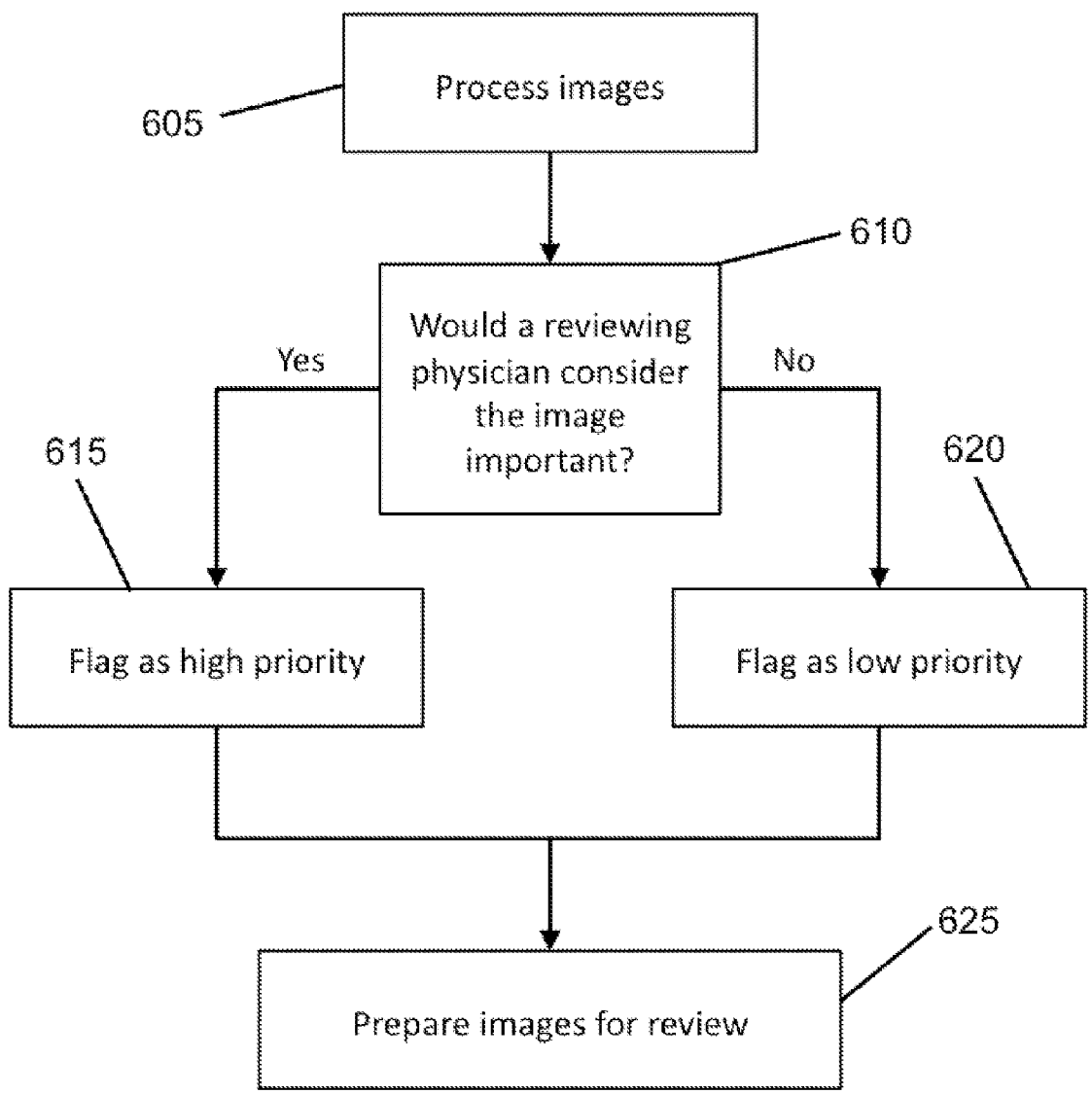
FIG. 6 shows a series of steps for prioritizing medical images, in accordance with an embodiment of the invention.

With reference to FIG. 6, in an embodiment of the invention, a method for prioritizing an image from an imaging modality is provided. In a first step 605, the PAPVR system retrieves images for review. Next, in step 610, the PAPVR system determines whether a reviewing or treating physician, such as a radiologist, would consider each image important. In an embodiment, step 610 can entail comparing each image to images from patients with known conditions to determine whether there is a match. In an embodiment, the PAPVR system can access an image database for image comparison. If the image under review is found by the PAPVR system to be important, in step 615 that image can be flagged as a "high priority" image. If the image is not found to be important (or if it is found to be unimportant), in step 620 that image can be flagged as "low priority." Next, in step 625, the PAPVR system prepares the images for review by a reviewing or treating physician.

In an embodiment, the PAPVR system can assign a priority value to an image based on the degree that the image matches one or more images from one or more patients with a known condition. Such matching can be accomplished by comparing the image under review by the PAPVR system to images from an image database. A higher priority value can be assigned to images that match known conditions (or physiological abnormalities) while a low priority can be assigned to images that do not match any known condition. For example, if an image under review matches an image from a patient with tension pneumo-thorax, that image can be assigned a high priority value. In some cases, a reverse priority value can be assigned, in which case a priority value is assigned based on the degree to which a given image matches one or more images from patients with no known conditions.

Case Prioritization

In another aspect of the invention, the PAPVR system can automatically prioritize patient cases. In various embodiments, the PAPVR system can automatically identify various medical conditions and assign that case a certain priority. The priorities assigned to the cases can be relative priorities (i.e., the PAPVR system determines that one case is of higher priority relative to another case in the queue of cases for a reviewing physician). Alternatively, the PAPVR system can prioritize cases based on absolute priority, which can entail prioritizing cases with patients having life-threatening conditions as high priority cases and patients without life-threatening conditions as low priority cases. The rules used by the PAPVR system to determine case priorities are configurable by the reviewing physician and the medical institution.

In an embodiment, the PAPVR system can automatically review a patient's images to determine whether the patient requires immediate medical care. If the PAPVR system determines that the patient requires immediate medical care, the PAPVR system can flag the patient's case as high priority. Otherwise, the PAPVR system can flag the patient's case as a lower priority (e.g., medium priority, low priority) case.

Figure 7:
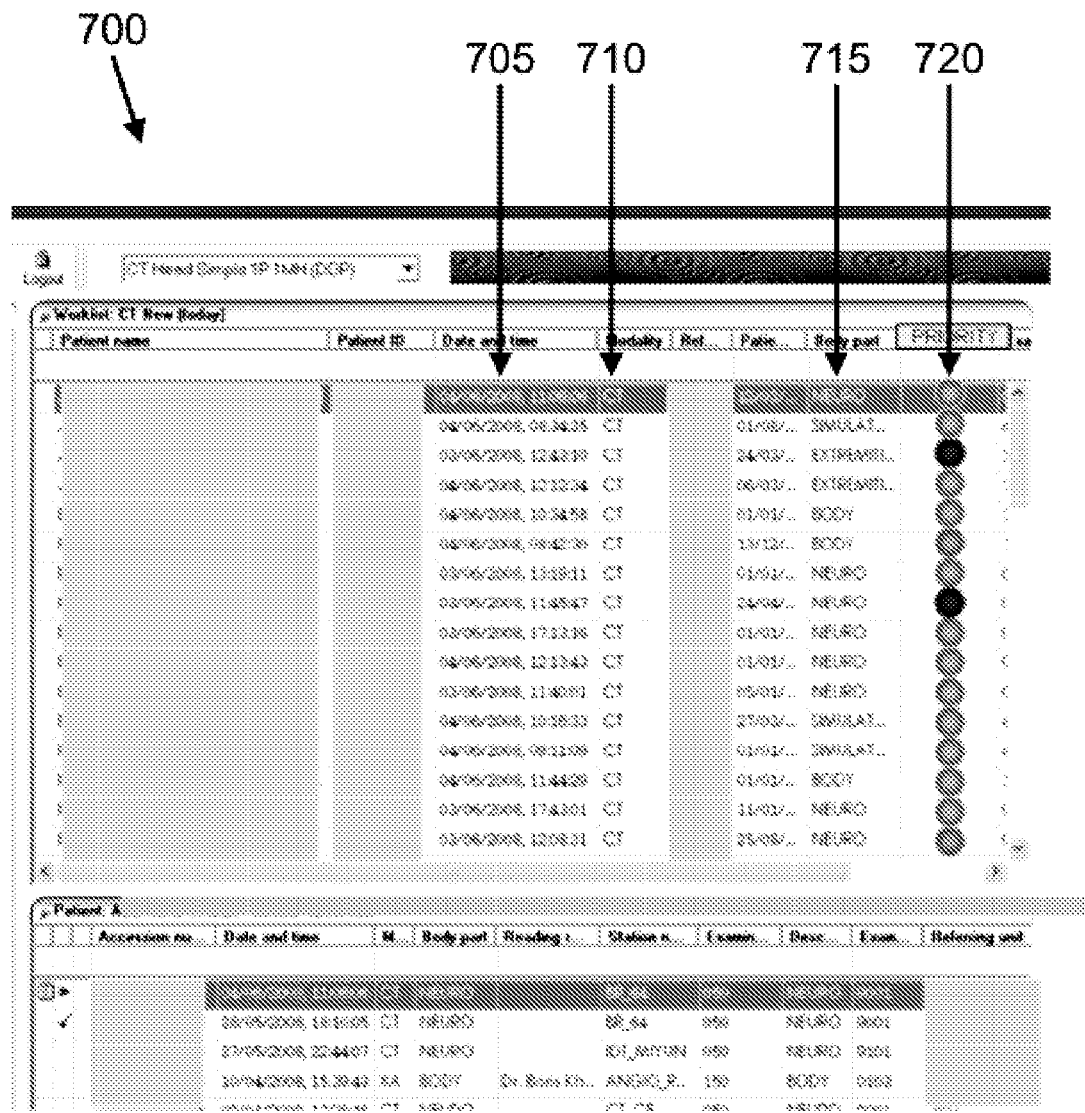
FIG. 7 is a screenshot of a patient case queue and the indication of priority of each case in the queue, in accordance with an embodiment of the invention.

With reference to FIG. 7, a screenshot of a patient case queue for a reviewing physician 700 is shown. The case queue includes a column 705 having a date and time stamp for each case, a column 710 with the modality (e.g., CAT/CT scan, MRI, PET/CT scan) used to acquire images, a column 715 showing the body part associated with each case, and a column 720 showing the priority associated with each case. The priority for each case can be indicated by a colored circle, with the color red indicating high priority, the color orange indicating medium priority, and the color green indicating low priority. Alternatively, the priority for each case can be indicated by a numerical value (e.g., 1-10, 1-100, 1-1000).

In an embodiment of the invention, the PAPVR system can automatically update case priorities. This can advantageously enable a reviewing physician, such as a radiologist, to be aware of the highest priority cases, such that these cases are reviewed first by the reviewing physician, and thus enable the referring or treating physician to get the reviewing physician's report sooner than if all cases were assigned the same priority. This capability of the PAPVR system can significantly shorten the time interval between when a patient is tested (e.g., with a CAT/CT scan, MRI, PET/CT scan) and when a patient is treated by the referring or treating physician after receiving the report from the reviewing physician. For example, if a case queue (such as queue 700 of FIG. 7) includes 10 cases with 1 case having high priority, 5 cases having medium priority and 4 cases having low priority, after the high priority case has been reviewed, the PAPVR system can reclassify the 9 remaining cases. This might entail reprioritizing the cases. In such fashion, the priorities assigned to the cases might be relative priorities (i.e., one case is of higher priority relative to another case). Alternatively, the PAPVR system can prioritize cases based on absolute priority, which might entail prioritizing cases with patients having life-threatening conditions as high priority cases.

In embodiments, the PAPVR can optionally sort cases by priority. In an embodiment, the PAPVR system can sort cases in descending order based on priority. For example, the PAPVR system can display high-priority cases at the top of the queue and low priority cases at the bottom of the queue.

Case Review and Reporting

In an aspect of the invention, the PAPVR system can provide one or more images associated with a particular patient, in addition to data associated with each image, to a radiologist (or other reviewing physician) for review. In a preferable embodiment, the PAPVR system provides a radiologist an assessment of each image. In an embodiment, the PAPVR system can determine whether a particular ailment or abnormality is present in an image, and provide its assessment (e.g., "A pleural effusion has been detected") to a reviewing physician. The PAPVR system of preferable embodiments of the invention can enable improved patient outcomes and increased productivity.

Figure 8:
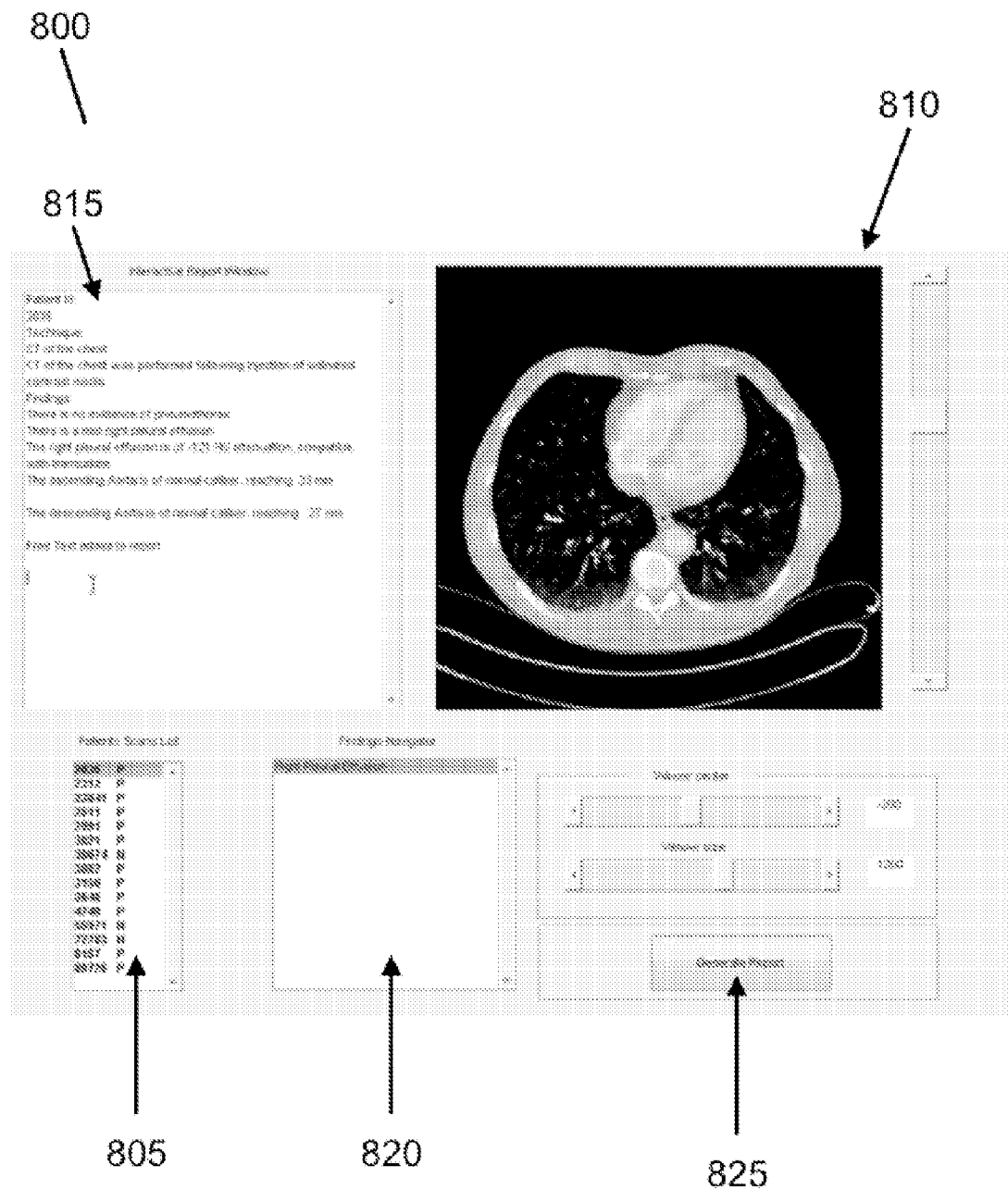
FIG. 8 is a screenshot of an interactive window, in accordance with an embodiment of the invention.

FIG. 8 an interactive window 800 that enables a radiologist to review images associated with each case, in addition to data provided by the PAPVR system. The interactive window 800 can also permit a radiologist to provide notes, including her/his assessment of the patient's condition. With continued reference to FIG. 8, the interactive window 800 includes a case or scan selection panel (or list) 805, a window 810 for displaying an image selected from the panel 805, an interactive report window 815 with information relevant to each image in the image window 810, a findings navigator window 820 that indicates the ailments or conditions (e.g., right pleural effusion) identified by the PAPVR system for the reviewed scan, and menu features 825 to permit a radiologist (or other reviewing physician) to generate a report and change the image visualization parameters (e.g., contrast or brightness), resize and center the window 810. The interactive report window 815 can include the patient's identification ("ID") number, the modality (CAT/CT scan, MRI, PET/CT scan) used to acquire the images, and the PAPVR system's assessment of the patient's condition. The interactive report window 815 can include other information, such as whether the priority associated with the patient's case, whether the image displayed in the window 810 is a Key Image, and whether the image displayed in the window 810 is a high priority image. The interactive report window 815 also permits a radiologist to provide additional information, such as additional findings with respect to the image shown in the window 810, and to edit the information provided by the PAPVR system.

In various embodiments, the findings navigator window 820 can be used by the reviewing physician to quickly navigate to and visualize in the image display window 810 Key Images the PAPVR system automatically associated with each of the findings that are listed in the findings navigator window 820. The PAPVR system can automatically adjust the visualization parameters of the image (e.g., contrast, brightness), or part of the image (e.g., highlighting the body organ in which an ailment was detected by the PAPVR system) displayed in the image display window 810 to help the reviewing physician better see or visualize the particular finding or findings.

In an embodiment, a PAPVR system prioritizes cases and provides the cases for review by a reviewing physician, such as a radiologist. The radiologist can use a computer terminal in communication with the PAPVR system to select the case of highest priority from the case queue (such as case queue 700 of FIG. 7). In an embodiment, the radiologist can use a reviewing system, such as the reviewing system 320 of FIG. 3, to retrieve a case. Next, the PAPVR system provides the radiologist an interactive window (such as interactive window 800 of FIG. 8) with images (e.g., two-dimensional cross-sections) from a particular region of a patient's body. In the interactive window the PAPVR system can provide its assessment of the patient's condition. The PAPVR system can permit the radiologist to provide additional information to the patient's case. The PAPVR system can also provide a radiologist additional information relevant to a particular image, such as distances, cross-sectional areas, and volumes.

Figure 9:
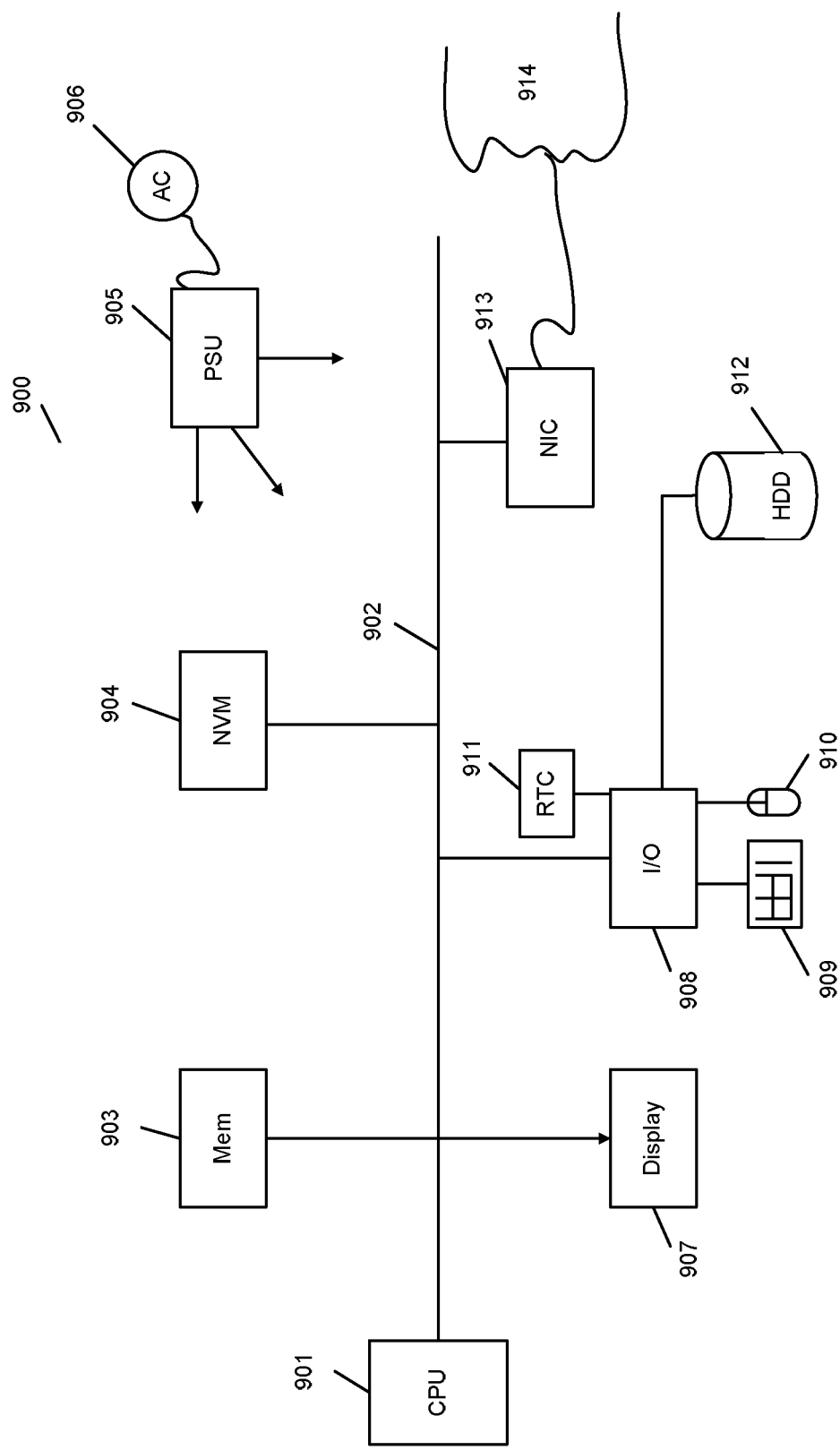
FIG. 9 is an exemplary overview of a computer system as may be used in any of the various locations throughout the system and method disclosed herein.

With reference to FIG. 9, a computer system 900 is exemplary of any computer that may execute code to process data. Various modifications and changes may be made to computer system 900 without departing from the broader spirit and scope of the system and method disclosed herein. CPU 901 is connected to bus 902, to which bus is also connected to memory 903, nonvolatile memory 904, display 907, I/O unit 908, and network interface card (NIC) 913. I/O unit 908 may, typically, be connected to keyboard 909, pointing device 910, hard disk (or in some cases other suitable storage, including, but not limited to solid state disk, RAID, network attached storage, storage area network, etc. 912, and real-time clock 911. NIC 913 connects to network 914, which may be the Internet or a local network, which local network may or may not have connections to the Internet. Also shown as part of system 900 is power supply unit 905 connected, in this example, to ac supply 906. Not shown are batteries that could be present, and many other devices, including but not limited to special enhanced pointing or navigational devices, such as mice, jog wheels, etc, microphone(s) and speaker(s) and/or headset(s) for recording and or playing back audio, and other modifications that are well known but are not applicable to the specific novel functions of the current system and method disclosed herein.

Figure 10:
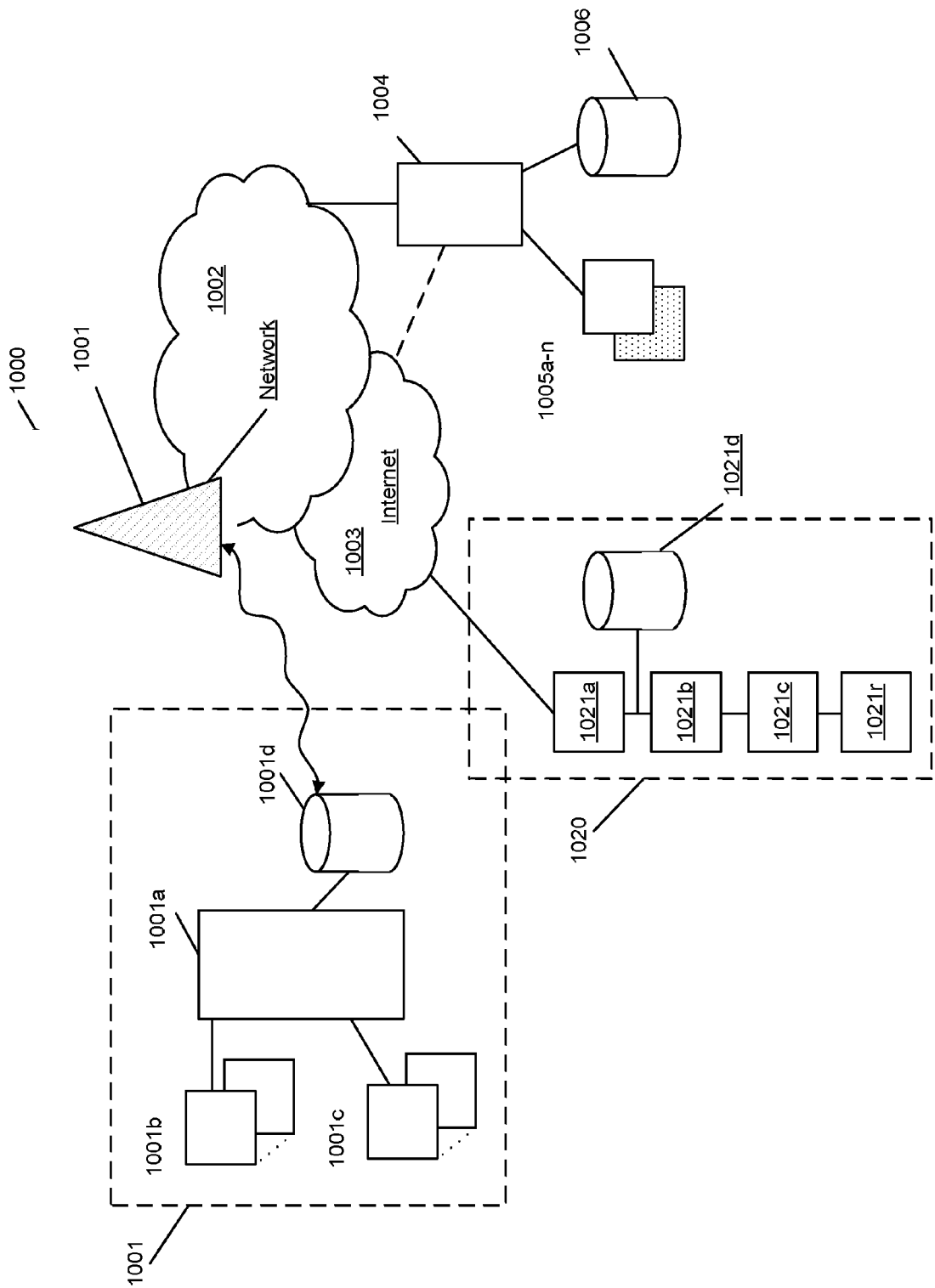
FIG. 10 is an exemplary overview of a network-based system, in accordance with an embodiment of the invention.

FIG. 10 shows a simplified overview of an exemplary PAPVR system 1000 in an Internet- or other network-based implementation, according to one aspect of the system and method disclosed herein. In an embodiment of the invention, the PAPVR system can be seen as a software 1005x running on server 1004 connected to a network 1002 (the Internet or a private network, or combination), having a local repository 1006, as well as additional software instances 1005a-n including such as operating system, networking software, image processing software and any other suitable or needed software. The system presents all images acquired from an imaging modality (e.g., CAT/CT scan 1021a, MRI 1021b, PET/CT scan 1021c, etc.) in one exemplary location in a hospital 1020 to a reviewing physician at a terminal or computing device 1021r in said hospital. In this example, the PAPVR is off site, and the physician views images in the hospital, but processing may happen off site. Additionally, patient data may be encrypted, so patient confidentiality is protected, etc. In an embodiment, the PAPVR system can first present the reviewing physician with the one or more Key Images (and data associated with the one or more representative images) and provide the reviewing physician the option to review the other (i.e., non-representative) images. In an embodiment, the non-representative images (and data associated with the non-representative images) can be viewed after the reviewing physician has viewed the one or more Key Images. By prioritizing transmission of key images, valuable minutes in an emergency room can be saved, for example. Also shown is a local storage 1021d.

Exemplary hospital 1001 may be in a remote location and use wireless communication to provide the same services to its physicians and patients, etc., having the same or similar equipment 1001a-n, analogous to 1021a-n.

Figure 11:
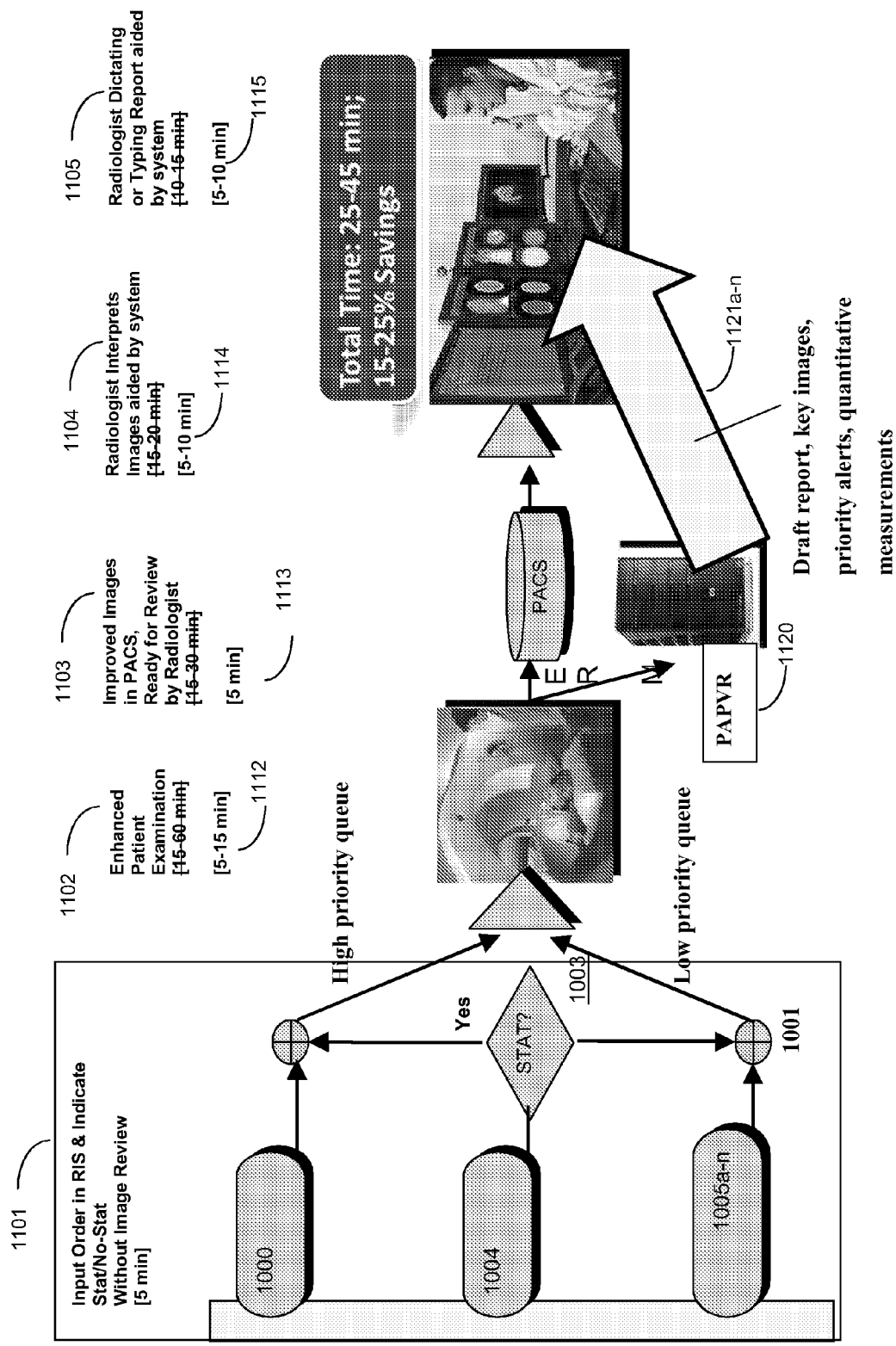
FIG. 11 is an exemplary revised timeline for the medical imaging workflow shown in FIG. 1, in accordance with an embodiment of the invention.

FIG. 11 shows an enhanced work flow with work times amended from those in FIG. 1, showing the time savings for steps for enhanced steps 1102, 1103, 1104 and 1105, which are analogous to, but improved as described herein, steps 102, 103, 104 and 105 of FIG. 1, with respectively revised times 1112, 1113, 114, and 1115. The PAPVR system 1120 generates items 1121a-n for the physician and other medical personnel.

In some other embodiments, the PAPVR system may present the reviewing physician the images in order of priority. In some embodiments, only the higher priority images may be displayed to the reviewing physician. Alternatively, all of the images, starting with the higher priority images may be displayed to the physician.

In some embodiments, the system may use a Key Image, or a high priority image to assist a physician with generating a report. In some embodiments, the default images for a report may be Key Images. A physician may be presented with the option of changing the image for the report. Alternatively, the physician may make an initial selection of the image(s) to be included within the report. This may help streamline the medical review process, and the report generation process.

While various embodiments of the invention have made reference to a "scan" or "scans," it will be appreciated that any use or reference to a "scan" or "scans" can refer to any type of image. As an example, a "scan" can refer to a medical image or a diagnostic image. As another example, "scans" can refer to multiple medical images.

It will be appreciated that PAPVR systems and methods of various embodiments of the invention can be integrated in (or used with) other systems and/or methods, such as, for example, medical or diagnostic systems and/or methods, both in part or in whole.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of embodiments of the invention herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A computer-implemented method for providing medical diagnostic images, comprising:
    using a computer system to retrieve a set of images from an image database or an imaging device, wherein the set of images includes images from a patient;
    using the computer system to determine whether each of the images of the patient is of medical interest to a reviewing physician based on whether each of the images deviates from a threshold value or shows any abnormality compared to a normalized version of a region of the image;
    using the computer system to determine a localization region of the image based on the set of images from the patient;
    using the computer system to determine whether one or more of the images is a representative image of the set of images of the patient, which representative image is determined to best capture a medical condition of the patient among other images of the set of images; and
    providing the images to a display and analysis system for review by the reviewing physician, wherein the images are provided with the representative image, wherein a localization region of the image is highlighted.

2. The computer-implemented method of claim 1, wherein determining whether each of the images is of medical interest to the reviewing physician includes providing an indication of the localization region of at least one area of interest.

3. The computer-implemented method of claim 2, further comprising using the computer system to flag each of the images as high priority or low priority.

4. The computer-implemented method of claim 2, further comprising using the computer system to prioritize the images.

5. The computer-implemented method of claim 4, wherein using the computer system to prioritize the images comprises comparing each of the one or more images to images from patients with known medical conditions.

6. The computer-implemented method of claim 5, wherein the images are prioritized based on the degree that each image matches the images from patients with known medical conditions.

7. A computer-implemented method for providing enhanced report capabilities for medical diagnostic images, comprising:
    from an image database or an imaging device, retrieving a set of images including images from a patient;
    determining whether each of the images is of medical interest to a reviewing physician based on whether each of the images deviates from a threshold value or shows any abnormality compared to a normalized version of a region of the image;
    determining a representative image that is representative of the set of images of the patient, which representative image is determined to best capture a medical condition of the patient;
    providing the images to a display and analysis system for review by the reviewing physician;
    providing one or more text blocks associated with images that are determined to be of medical interest to the reviewing physician; and
    providing the one or more text blocks associated with the images and the images for the reviewing physician to mix, match and edit the one or more text blocks to create a report for review by a referring physician.

8. The method of claim 7, wherein the one or more text blocks are for permitting a reviewing physician to record instructions for another person to edit and mix and match the one or more text blocks.

9. The method of claim 7, wherein determining whether each of the images is of medical interest to a reviewing physician includes providing quantitative measurements.

10. The method of claim 7, wherein determining whether each of the images is of medical interest to a reviewing physician includes providing an indication of the localization of at least one area of interest.

11. The method of claim 7, wherein determining whether one or more of the images is a representative image comprises flagging an image as a key image.

12. The method of claim 7, further comprising performing quantitative measurements and calculations after retrieving the images from the image database or the imaging device.

13. The method of claim 7, further comprising prioritizing the images.

14. The method of claim 13, further comprising flagging each of the images as high priority or low priority based on the degree to which the images deviate from the threshold value.

15. The method of claim 13, wherein prioritizing the images comprises comparing each of the images to images from patients with known medical conditions.

16. The method of claim 15, wherein the images are prioritized based on the degree that each image matches the images from patients with known medical conditions.

17. A system for visualizing and reporting patient-specific medical information, comprising:

an imaging modality for retrieving medical diagnostic images from a patient;

a reviewing system for displaying medical images to a reviewing physician;

a prioritization, visualization and reporting system in communication with the imaging modality and the reviewing system, wherein the prioritization, visualization and reporting system is for:

from the imaging modality, retrieving a set of images including images from a patient;

determining whether each of the images is of medical interest to a reviewing physician based on whether each of the images deviates from a threshold value or shows any abnormality compared to a normalized version of a region of the image;

determining a representative image among the images that is representative of the set of images, which representative image is determined to best capture a medical condition of the patient among other images of the set of images; and providing the images to the reviewing system for displaying the images and the representative image to the reviewing physician.

18. The system of claim 17, wherein the prioritization visualization and reporting system is for prioritizing the images in the set of images.

19. The system of claim 17, wherein the prioritization visualization and reporting system is in communication with a picture archiving communication system.

20. The system of claim 17, wherein the prioritization visualization and reporting system automatically prioritizes the images based on the degree that each image matches an image from the individual with the known medical condition.

* * * * *